US007858377B2

(12) United States Patent
Komissarova et al.

(10) Patent No.: US 7,858,377 B2
(45) Date of Patent: Dec. 28, 2010

(54) METHOD FOR PREPARING A QUALITY CONTROL MIXTURE FOR GLYCINE TABLETS

(75) Inventors: Irina Alekseevna Komissarova, Moscow (RU); Tatyana Dmitrievna Soldatenkova, Moscow (RU); Yulia Vasilievna Gudkova, Zelenograd (RU); Tatyana Tikhonovna Kondrashova, Moscow (RU); Natalia Mikhaylovna Burbenskaya, Moscow (RU)

(73) Assignee: Nekommercheskoe Uchrezhdenie "Nauchno-Issledovateljskiyj Institut Citokhimii I Molekulyarnoyj Farmakologii", Moscow (RU)

( * ) Notice: Subject to any disclaimer, the term of this patent is extended or adjusted under 35 U.S.C. 154(b) by 0 days.

(21) Appl. No.: 12/097,047

(22) PCT Filed: Dec. 15, 2006

(86) PCT No.: PCT/RU2006/000674

§ 371 (c)(1),
(2), (4) Date: Dec. 5, 2008

(87) PCT Pub. No.: WO2007/075124

PCT Pub. Date: Jul. 5, 2007

(65) Prior Publication Data

US 2009/0124018 A1 May 14, 2009

(30) Foreign Application Priority Data

Dec. 16, 2005 (EA) ................................ 200600147

(51) Int. Cl.
*G01N 33/00* (2006.01)
*A01N 37/12* (2006.01)

(52) U.S. Cl. ........................................ 436/89; 514/561

(58) Field of Classification Search .................... 436/89
See application file for complete search history.

(56) References Cited

U.S. PATENT DOCUMENTS

| | | | | |
|---|---|---|---|---|
| 5,534,262 | A * | 7/1996 | Dobrotvorsky et al. ...... | 424/464 |
| 5,643,954 | A * | 7/1997 | Komissarova et al. ....... | 514/561 |
| 5,731,349 | A * | 3/1998 | Komissarova et al. ....... | 514/561 |
| 2004/0029966 | A1* | 2/2004 | Komissarova ............... | 514/561 |

OTHER PUBLICATIONS

Ahmed et al. ("Quality of Marketed Metronidazole Preparations in Bangladesh—An Analytical Overview," J. Biol. Sci. 2003, 3, 940-950).*

* cited by examiner

*Primary Examiner*—Yelena G Gakh
*Assistant Examiner*—Michelle M Adams
(74) *Attorney, Agent, or Firm*—Houston Eliseeva, LLP

(57) ABSTRACT

A method is described for preparing a mixture for quality control of 0.1 g glycine tablets for sublingual application. The mixture for quality control includes a 100:1 ratio of water to porphyrized tablets, each tablet containing 0.101 g microcapsules of non-agglomerated crystals of amino-acetic acid covered with polymeric film of water-soluble methylcellulose, each tablet further comprising 0.001 g magnesium stearate. The process of dissolution takes 20 minutes and is carried out at a temperature of 37° C. in an apparatus using a paddle rotation speed of 150 revolutions per minute. After the mixture is dissolved, it is allowed to stand for 10 minutes, then a light transmission coefficient is measured at 700±2 nm for a 10 mm thick layer of the mixture. A transmission value within the range of 50% to 70% compared to purified water corresponds to the proper quality.

1 Claim, No Drawings

METHOD FOR PREPARING A QUALITY CONTROL MIXTURE FOR GLYCINE TABLETS

CROSS-REFERENCES TO RELATED APPLICATIONS

This application is a National Stage of International Application No. PCT/RU2006/000674, filed Dec. 15, 2006, claiming priority to Eurasian Patent Application EA 200600147, filed Dec. 16, 2005.

FIELD OF APPLICATION

The invention relates to the chemical-pharmaceutical industry and specifically to mix for quality control of the medicine "Glycine tablets for sublingual applying 0.1 g." and its preparation method.

BACKGROUND OF INVENTION

The medicine "Glycine tablets for sublingual applying 0.1 g." is produced on the base of amino-acetic acid contained in all body cells. Amino-acetic acid is a broad-spectrum metabolite. The drug activates inhibitory processes in central nervous system, it has stressprotective and antistress effect and contributes to the increase of mental capacity.

For medicine production (tablets 0.102 g±7.5%) microcapsules of non-agglomerated crystals of amino-acetic acid covered with water-soluble methylcellulose, MC-100 (wherein MC-100 is a water-soluble methylcellulose having a dynamic viscosity in a 1% water solution (by mass) greater than 0.08 Pa·s, having a methoxy group content of 26-33% by mass, having a water solubility at least 98%, having an ash content no greater than 0.3% by mass, and having a water content no greater than 6% by mass), and magnesium stearate are used.

The pharmacopeia (FC 42-3491-98) comprises a range of tests for quality control of the medicine "Glycine tablets for sublingual applying 0.1 g." with stressprotective, antistress, nootropic and neuroprotective effect for single or longterm administration in the form of a tablet applied sublingually, containing amino-acetic acid (0.100 g.), water-soluble methylcellulose, MC-100 (0.001 g.) and magnesium stearate (0.001 g.) with a mass of 0.102 g.±7.5% and decomposition period varying from 10 to 30 minutes.

There is analysed identity, mass average, decomposition period, foreign substances, microbiologic purity, quantitative content of amino-acetic acid.

It is commonly known that for identity check there is dissolved 0.05 g. of porphyrized tablets in 50 ml of water for 2 minutes. There is added 0.2 ml. of ninhydrin dissolved in acetone to 10 ml. of the obtained solution and heated up to the appearance of blue-purple colouration.

The stain on the medicine chromatogramme obtained in the test of foreign substances must be on one level with the witness standard substance.

Amino-acetic acid quantitation is enhanced by titration.

The medicine "Glycine tablets for sublingual applying 0.1 g." like other solid dosage forms produced by various enterprises with equal dosage of a medicine (pharmacologically active substance) and equal content and identity of adjunct (auxiliary) components can differ greatly by pharmacological effect (therapeutic effect).

These differences are caused by technology factors: pulverizing, humidification, microcapsulation, thermal drying, compression parameters which together as well as separately can induce polymorphous modification of medicinal substance.

In particular, compression influences greatly particles specific surface and size modification by elastic and plastic deformation, partial destruction of the compressed material and phase contacts mainly.

The essential factor able to increase or decrease activity of active substances and dosage forms is adjunct ingredients. It is determined by the fact that adjuncts have definite physico-chemical characteristics which can be revealed in different ways depending on conditions. On stages of technology process while obtaining solid dosage forms there can be traced physico-chemical interactions between initial components able to change activity of the medicine and add new functions to adjunct components. Such phenomenon changes the concept about indifference of adjuncts and requires some corrections in the approaches to the drugs quality control, comprising not only determination of the medicine content, its decomposition and dissolving period but also analysis of physico-chemical interaction of medical and adjunct substances in aqueous medium and biologic fluid inclusively. Not only the release rate of active substance but also the intensity degree of pharmacological effect depends on interaction of solid dosage form components (Tentsova A. I., Azhrukhin I. S., "The Dosage Form and Therapeutic Efficacy. (Introduction into Bioinformation)", Moscow, "Medicine", 1974, pp. 107-122).

Thus, not only the dosage of a medical substance but also qualitative and quantitative content of auxiliary components can be modified uncontrollably. For modification control of quantitative and qualitative composition of auxiliary components and manufacturing technique there must be developed simple and accessible methods of investigation which provide discovering production violations as well as pharmaceutical ones in the process of certification.

The means and methods of quality control of the medicine "Glycine tablets for sublingual applying 0.1 g." envisaged by the pharmacopeia (FC 42-3491-98) do not make it possible to check if qualitative and quantitative content of adjuncts corresponds to the obtained one, if the drug preparation technique is observed involving the use of microcapsules in the form of a fraction of active component and lubricating component, magnesium stearate. Therefore, it is impossible to guarantee that the medicine produced provides necessary therapeutic effect, since even considerable deviations of composition and technique in preparation of the medicine "Glycine tablets for sublingual applying 0.1 g." are not discovered by the known control methods envisaged by the pharmacopeia (FC 42-3491-98).

BRIEF SUMMARY OF THE INVENTION

The major focus of the present complex of inventions is on elaboration of quality control means and on control of observation of the medicine "Glycine tablets for sublingual applying 0.1 g." endowed with stressprotective, antistress, nootropic and neuroprotective effect, used in the form of sublingual tablets of 0.1 g containing microcapsuled glycine—non-agglomerated crystals of amino-acetic acid covered with polymeric film of water-soluble methylcellulose, MC-100 and magnesium stearate.

There is set the task of composition identity evaluation (which is usually achieved by qualitative and quantitative determination of each component), i.e. the task of quantitative examination of tablet qualitative composition, taking into account the interaction character of medicinal substance and adjunct components in aqueous medium.

New quality control means must complete the known quality control methods of "Glycine tablets for sublingual applying 0.1 g." already applied which together with new means must demonstrate that they meet medicine quality requirements providing its optimum efficacy.

It is evident that control methods must be simple and must envisage the use of accessible facilities.

The given tasks are being accomplished in the following way: mix for quality control of the medicine "Glycine tablets for sublingual applying 0.1 g." in the form of tablets containing microcapsuled glycine—non-agglomerated crystals of amino-acetic acid covered with polymeric film of water-soluble methylcellulose, MC-100 and magnesium stearate with decomposition period varying from 10 to 20 minutes, crushing resistance ranging from 10 to 30 N, involves water and porphyrized tablets in a ratio 100:1, the latter containing 0.98%±7.5% of amino-acetic acid, 0.01%±7.5% of water-soluble methylcellulose, MC-100 and 0.01%±7.5% of magnesium stearate. Light transmission coefficient of 4 ml. mix with layer thickness of 10 mm and wave length of 700±2 nm in comparison with purified water is within the limits of 50% to 70%.

Mix preparation method comprises dissolving of 2.5 g of porphyrized tablets in 250 ml of purified water for 20 minutes at 37° C. in an apparatus for dissolving determination at a paddle rotation speed of 150 rpm. Then mix is allowed for 10 minutes, 4 ml are selected and subjected to spectrophotometer examination for light transmission at a wave-length of 700±2 nm in a cuvet with layer thickness of 10 mm relative to purified water.

DETAILED DESCRIPTION OF THE INVENTION

Quality control of the medicine "Glycine tablets for sublingual applying 0.1 g." for each batch is carried out in laboratories of quality control departments in pharmaceutical companies and in test laboratories of certification centres.

First there is prepared the mix by dissolving of 2.5 g of porphyrized tablets in 250 ml of purified water. At a temperature of 37° C. the process of dissolving is carried out for 20 minutes in the "Erweka"-type paddle for dissolving determination at a rotation speed of 150 rpm.

Then mix is allowed for 10 minutes, 4 ml are selected and measured on spectrophotometer for light transmission at a wave length 700±2 nm in a cuvet with layer thickness of 10 mm relative to purified water.

Light transmission value within the range of 50%-70% corresponds to the medicine "Glycine tablets for sublingual applying 0.1 g." of the proper quality with necessary therapeutic effect containing 0.100 g of amino-acetic acid, 0.001 g of water-soluble methylcellulose, MC-100, 0.001 g of magnesium stearate.

Quality analysis of the medicine active ingredients, amino-acetic acid is carried out on the stage of identity control.

There is selected 1 ml of the obtained base mix before its allowance, then there are added 9 ml of purified water and 0.2 ml of ninhydrin dissolved in acetone (0.85 g of ninhydrin in 50 ml of acetone). The composition is heated till the appearance of blue-purple colouration.

The stain on chromatogramme corresponding to the amino-acetic acid obtained in medicine test of foreign substances must be on one level with the standard glycine sample.

Other stages of control are held according to standard methods. There is tested tablets decomposition period which must be confined to the limits of 10-20 minutes, and tablets crushing resistance.

The interaction confirmation of the "Glycine tablets for sublingual applying 0.1 g." determinate quality content and light transmission value is demonstrated in the table presenting the analysis results made in accordance with the below examples.

Example 1

2.5 g of the "Glycine tablets for sublingual applying 0.1 g." were dissolved in 250 ml of water for 20 minutes at 37° C. in the apparatus for dissolving determination, paddle "Erweka" at a paddle rotation speed of 150 rpm.

Decomposition period of tablets with mottle elements varied from 10 to 20 minutes, resistance ranged from 10 to 30N. The tablets contained 0.1±7.5% amino-acetic acid, 0.001±7.5% of water-soluble methylcellulose, MC-100 and 0.001±7.5% of magnesium stearate, in one tablet.

On complete dissolution of the tablets within 20 minutes mix was allowed for 10 minutes, then there were selected 4 ml of mix in a cuvet with layer thickness of 10 mm and later subjected to spectrophotometer examination versus solvent (purified water) at a wave length of 700±2 nm.

Light transmission coefficient was 65%.

Example 2

2.5 g of the porphyrized "Glycine tablets for sublingual applying 0.1 g." were dissolved in 250 ml of water for 20 minutes at a temperature of 37° C. in the dissolving determination apparatus "Erweka"-type paddle at a rotation speed of 150 rpm.

After the tablets were dissolved for 20 minutes mix was allowed for 10 minutes, then 4 ml were selected and examined in spectrophotometer versus solvent (purified water) at a wave length of 700±2 nm in a cuvet with 10 mm layer thickness.

Transmission coefficient was 63%.

Example 3

1.25 g of the porphyrized "Glycine tablets for sublingual applying 0.1 g." was dissolved according to the run of example 2 and examined in spectrophotometer.

Transmission coefficient was 79%.

Example 4

5 g of the porphyrized "Glycine tablets for sublingual applying 0.1 g." were dissolved in a way similar to example 2 and examined in spectrophotometer.

Transmission coefficient was 37%.

Example 5

2.5 g of porphyrized tablets, containing 0.099 g of amino-acetic acid, 0.002 g of methylcellulose and 0.001 g of magnesium stearate in a tablet, were dissolved and investigated in spectrophotometer in a way similar to in example 2.

Transmission coefficient was 79%.

Example 6

2.5 g of porphyrized tablets containing 0.1 g of amino-acetic acid, 0.001 g of carboxymethylcellulose and 0.001 g of magnesium stearate in one tablet, were dissolved and subjected to spectrophotometer examination according to the run of example 2.

Light transmission coefficient was 75-85%.

Example 7

2.5 g of porphyrized tablets containing 0.1 g of amino-acetic acid, 0.001 g of water-soluble methylcellulose, MC-100 and 0.001 g of calcium stearate in one tablet, were dissolved and examined on spectrophotometer in a way similar to example 2.

Light transmission coefficient was 45%.

TABLE

| Example No | Qualitative content | Quantitative content, % ± 7.5% | Light transmission coefficient, % |
|---|---|---|---|
| 1 | amino-acetic acid | 0.98 | 65 (60 ± 16.6) |
| | water-soluble methylcellulose, MC-100 | 0.01 | |
| | magnesium stearate | 0.01 | |
| | water | the rest | |
| 2 | amino-acetic acid | 0.98 | 63 (60 ± 16.6) |
| | water-soluble methylcellulose, MC-100 | 0.01 | |
| | magnesium stearate | 0.01 | |
| | water | the rest | |
| 3 | amino-acetic acid | 0.49 | 79 (75 ± 5) |
| | water-soluble methylcellulose, MC-100 | 0.005 | |
| | magnesium stearate | 0.005 | |
| | water | the rest | |
| 4 | amino-acetic acid | 1.96 | 37 (36 ± 10) |
| | water-soluble methylcellulose, MC-100 | 0.02 | |
| | magnesium stearate | 0.02 | |
| | water | the rest | |
| 5 | amino-acetic acid | 0.97 | 78 (75 ± 5) |
| | water-soluble methylcellulose, MC-100 | 0.02 | |
| | magnesium stearate | 0.01 | |
| | water | the rest | |
| 6 | amino-acetic acid | 0.98 | 80 (80 ± 6) |
| | carboxymethylcellulose | 0.01 | |
| | magnesium stearate | 0.01 | |
| | water | the rest | |
| 7 | amino-acetic acid | 0.98 | 45 |
| | water-soluble methylcellulose, MC-100 | 0.01 | |
| | calcium stearate | 0.01 | |
| | water | the rest | |

The invention claimed is:

1. A method of preparing a mixture for quality control of 0.1 g glycine tablets for sublingual application, the tablets having stress-preventative, anti-stress, nootropic, and neuroprotective effects, the tablets being suitable for single administration or for long-term treatment, each tablet comprising microcapsulated glycine comprising non-agglomerated crystals of amino-acetic acid covered with a polymeric film of water-soluble methylcellulose, each tablet further comprising magnesium stearate, each tablet having a crush resistance of at least 10 N and no more than 30 N, the method comprising:

providing said tablets that have been porphyrized;

obtaining the mixture by mixing 2.5 g of porphyrized tablets in 250 mL purified water for 20 minutes at a temperature of 37° C. in an apparatus using a paddle rotation speed of 150 revolutions per minute;

allowing the mixture to stand for 10 minutes; and measuring a light transmission coefficient of 4 mL of the mixture for a 10 mm thick layer in a container relative to the light transmission coefficient for purified water using a light transmission spectrophotometer at a wavelength of 700±2 nm.

* * * * *